(12) United States Patent
Showell et al.

(10) Patent No.: US 10,081,562 B2
(45) Date of Patent: Sep. 25, 2018

(54) MICROBIAL COMPOSITIONS AND METHODS FOR DENITRIFICATION AT HIGH DISSOLVED OXYGEN LEVELS

(71) Applicant: BiOWiSH Technologies Inc., Cincinnati, OH (US)

(72) Inventors: Michael S. Showell, Cincinnati, OH (US); John Gorsuch, Cincinnati, OH (US); Joseph Roberts, Cincinnati, OH (US)

(73) Assignee: BiOWiSH Technologies, Inc., Cincinnati, OH (US)

( * ) Notice: Subject to any disclaimer, the term of this patent is extended or adjusted under 35 U.S.C. 154(b) by 0 days.

(21) Appl. No.: 15/147,489

(22) Filed: May 5, 2016

(65) Prior Publication Data

US 2016/0326034 A1  Nov. 10, 2016

Related U.S. Application Data

(60) Provisional application No. 62/157,327, filed on May 5, 2015.

(51) Int. Cl.

| | | |
|---|---|---|
| C02F 3/34 | (2006.01) |
| C02F 3/02 | (2006.01) |
| C12N 1/20 | (2006.01) |
| C02F 3/00 | (2006.01) |
| C02F 3/10 | (2006.01) |
| C02F 101/16 | (2006.01) |

(52) U.S. Cl.
CPC ............. *C02F 3/341* (2013.01); *C02F 3/006* (2013.01); *C02F 3/02* (2013.01); *C02F 3/105* (2013.01); *C12N 1/20* (2013.01); *C02F 2101/163* (2013.01); *C02F 2209/001* (2013.01); *C02F 2209/15* (2013.01); *C02F 2209/22* (2013.01); *Y02W 10/15* (2015.05)

(58) Field of Classification Search
CPC ...................................................... C02F 3/341
See application file for complete search history.

(56) References Cited

U.S. PATENT DOCUMENTS

| | | |
|---|---|---|
| 5,627,069 A | 5/1997 | Powlen |
| 6,025,152 A | 2/2000 | Hiatt |
| 6,410,305 B1 | 6/2002 | Miller et al. |
| 7,037,708 B1 | 5/2006 | Runge et al. |
| 9,302,924 B1 | 4/2016 | Showell et al. |

(Continued)

FOREIGN PATENT DOCUMENTS

| | | |
|---|---|---|
| CN | 101473896 A | 7/2009 |
| CN | 101503664 A | 8/2009 |

(Continued)

OTHER PUBLICATIONS

Application Data Sheet 4950-01, Dissolved Oxygen Measurement in Wastewater Treatment, Water and Wastewater Industry, Emerson Process Management, http://www2.emersonprocess.com/siteadmincenter/PM%20Rosemount%20Analytical%20Documents/Liq_ADS_4950-01.pdf, 2009.*

(Continued)

*Primary Examiner* — Rosanne Kosson
(74) *Attorney, Agent, or Firm* — Cooley LLP; Ivor R. Elrifi; Cynthia A. Kozakiewicz

(57) ABSTRACT

The present invention provides compositions and methods for denitrification.

12 Claims, 3 Drawing Sheets

Specification includes a Sequence Listing.

(56) References Cited

U.S. PATENT DOCUMENTS

| | | | |
|---|---|---|---|
| 9,717,767 | B2 | 8/2017 | Carpenter et al. |
| 2003/0109025 | A1 | 6/2003 | Durand et al. |
| 2004/0042972 | A1 | 3/2004 | Truong-Le et al. |
| 2006/0188978 | A1 | 8/2006 | Grant |
| 2007/0060477 | A1 | 3/2007 | Pedersen et al. |
| 2007/0134493 | A1 | 6/2007 | Meghpara |
| 2008/0260923 | A1 | 10/2008 | Kratky et al. |
| 2009/0042267 | A1 | 2/2009 | Park |
| 2009/0269307 | A1 | 10/2009 | Albers et al. |
| 2011/0014278 | A1 | 1/2011 | Derrieu |
| 2011/0110894 | A1* | 5/2011 | Drahos ............ C02F 3/1268 424/93.3 |
| 2011/0269220 | A1 | 11/2011 | Van Slyke |
| 2012/0083412 | A1 | 4/2012 | Trevino et al. |
| 2012/0084886 | A1 | 4/2012 | Lopez-Cervantes et al. |
| 2013/0337518 | A1 | 12/2013 | Razavi-Shirazi et al. |
| 2014/0342437 | A1 | 11/2014 | Carpenter |
| 2016/0029666 | A1 | 2/2016 | Carpenter et al. |
| 2016/0312252 | A1 | 10/2016 | Carpenter et al. |

FOREIGN PATENT DOCUMENTS

| | | |
|---|---|---|
| CN | 101538538 | 9/2009 |
| CN | 102399733 A | 4/2012 |
| CN | 102987079 A | 3/2013 |
| CN | 103484413 A | 1/2014 |
| CN | 103087918 B | 4/2015 |
| DE | 19617331 A1 | 11/1997 |
| EP | 0410877 A1 | 1/1991 |
| EP | 0720974 A1 | 7/1996 |
| JP | 2001/299328 | 10/2001 |
| WO | WO 2001068808 A1 | 9/2001 |
| WO | WO 2006082328 A2 | 8/2006 |
| WO | WO 2009038530 A1 | 3/2009 |
| WO | WO 2010/138522 A2 | 12/2010 |
| WO | WO 2014/189963 A1 | 11/2014 |
| WO | WO 2015/056185 A1 | 4/2015 |
| WO | WO 2016/019017 A1 | 2/2016 |
| WO | WO 2016/073981 A1 | 5/2016 |

OTHER PUBLICATIONS

Downes et al., "Determination of Cyanuric Acid Levels in Swimming Pool Waters by u.v. Absorbance, HPLC and Melamine Cyanurate Precipitation", Water Res., vol. 18, No. 3, pp. 277-280, (1984).

Baetge et al. "Complete nucleotide and deduced amino acid sequence of bovine phenylethanolamine N-methyltransferase: Partial amino acid homology with rat tyrosine hydroxylase" Proc. Natl. Acad. Sci. USA, vol. 83, pp. 5454-5458, Aug. 1986.

O'Brien et al., "Equilibria in Aqueous Solutions of Chlorinated Isocyanurate", In A.J. Rubin, ed. Chemistry of Water Supply, Treatment, and Distribution, Chapter 14. Ann Arbor Science Publishers, Ann Arbor, Michigan (1974).

Shields et al., "Inactivation of Cryptosporidium parvum under chlorinated recreational water conditions", Journal of Water and Health, 06.4:513-520 (2008).

Shannon, M.A.; Bohn, P.W.; Elimelech, M; Georgiadis, J.G.; Marinas, B.J.; Mayes, A.M., Mar. 2008, Science and technology for water purification in the coming decades, Nature, 452 (7185), 301-310.

Schmidt, S.P.; Basolo, F.; Trogler, W.C., 1987, Reactions between dimanganese, dirhenium, and manganese-rhenium decacarbonyl and oxidants. Inorg. Chim. Acta, 131 (2), 181-189.

Koops, H.-P.; Pommerening-Roser, A., 2001, Distribution and ecophysiology of the nitrifying bacteria emphasizing cultured species, FEMS Microbiology Ecology, 37(1), 1-9.

Hommes, N.G.; Sayavedra-Soto, L.A.; Arp, D.J., 2003, Chemolithoorganotrophic Growth of Nitrosomononas eruopaea on Fructose. Journal of Bacteriology, 185 (23), 6809-6814.

Prosser, J.I., 1989, Autotrophic nitrification in bacteria. Advances in microbial physiology, 30, 125-181.

Tramper, J; Grootjen, D.R.J., 1986, Operating performance of Nitrobacter agilis immobilized in carrageenan. Enzyme and Microbial Technology 8 (8), 477-480.

Shapleigh, J., 2006, The Denitrifying Prokaryotes. In the Prokaryotes, Dworkin, M.; Falkow, S.; Rosenberg, E.; Schleifer, K.-H.; Stackebrandt, E., Eds. Springer New York; pp. 769-792.

Verbaendert, I.; Boon, N.; De Vos, P.; Heylen, K., 2011, Denitrification is a common feature among members of the genus Bacillus. Syst Appl Microbio 34 (5), pp. 385-391.

Strous, M.; Fuerst, J.A.; Kramer, E.H.; Logemann, S.; Muyzer, G.; van de Pas-Schoonen, K.T.; Webb, R.; Kuenen, J.G.; Jetten, M.S., 1999, Missing lithotroph identified as new planctomycete. Nature 400 (6743), 446-449.

Jetten, M.S.M., Wagner, M.; Fuerst, J.; van Loosdrecht, M.; Kuenen, G.; Strous, M., 2001, Microbiology and application of the anaerobic ammonium oxidation ('anammox') process. Current Opinion in Biotechnology, 12 (3), 283-288.

Hellinga, C.; Schellen, A.A.J.C.; Mulder, J.W.; van Loosdrecht, M.C.M.; Heijnen, J.J., 1998, The Sharon process; An innovative method for nitrogen removal from ammonium-rich waste water. Water Science and Technology, 37 (9), 135-142.

Third, K.A.; Sliekers, A.O.; Kuenen, J.G.; Jetten, M.S., 2001, the CANON system (Completely Autotrophic Nitrogen-removal Over Nitrite) under ammonium limitation; Interaction and competition between three groups of bacteria. Systematic and applied microbiology 24 (4), 588-596.

Schreiber, F., 2009, Detecting and Understanding Nitric Oxide Formation during Nitrogen Cycling in Microbial Biofilms. Universitaet Bremen, Bremen, 154 pages in total.

Schmidt, I.; Sliekers, O.; Schmid, M.; Bock, E.; Fuerst, J.; Kuenen, J.G.; Jetten, M.S.M.; Strous, M., 2003, New concepts of microbial treatment processes for the nitrogen removal in wastewater. FEMS Microbiology Reviews, 481-492.

Kim, J.K.; Park, K.J.; Cho, K.S.; Nam, S.-W.; Park, T.-J.; Bajpai, R., 2005, Aerobic nitrification-denitrification by heterotrophic Bacillus strains. Bioresource Technology, 96 (17), 1897-1906.

Hageman, J.H.; Shankweiler, G.W.; Wall, P.R.; Franich, K.; McCowan, G. W.; Cauble, S.M.; Grajeda, J.; Quinones, C., 1984, Single, chemically defined sporulation medium for Bacillus subtilis; growth, sporulation, and extracellular protease production. Journal of Bacteriology, 160 (1), 438-441.

Gude et al. "Biodiesel from waste cooking oils via direct sonication", Applied Energy, vol. 109, 2013, pp. 135-144.

Veljković et al. "Biodiesel production by ultrasound-assisted transesterification: State of the art and the perspectives" Renewable and Sustainable Energy Reviews, vol. 16, 2012, pp. 1193-1209.

Chan, Ada Mingwah "Investigation of Dairy Wastewater Using Biowish™", M. Sc. Thesis, Dec. 2014, pp. i-xv, 1-142, XP55289814, San Luis Obispo, CA, USA.

Lee, Eva "Investigation of a Commerical Product (Biowish™) for Nitrogen Management", M. Sc. Thesis, May 2012, pp. i-xix, 1-131, XP55290312, San Luis Obispo, CA, USA.

Roberts, M.S. et al. "*Bacillus mojavensis* sp. nov., Distinguishable from Bacillus subtilis by Sexual Isolation, Divergence in DNA Sequence, and Differences in Fatty Acid Composition", International Journal of Systematic Bacteriology, vol. 44, No. 2, Apr. 1994, pp. 256-264.

Deng, Bin et al. "The Denitrification Characteristics of Pseudomonas stutzeri SC221-M and its Application to Water Quality Control in Grass Carp Aquaculture", PLOS One, vol. 9, No. 12, Dec. 9, 2014, p. e114886.

Anonymous: "Biological Help for the Human Race Wastewater Treatment Solutions", 2011, pp. 1-12, Chicago, IL, USA.

Rajakumar, S. et al. "Nitrate removal efficiency of bacterial consortium (*Pseudomonas* sp. KW1 and *Bacillus* sp. YW4) in synthetic nitrate-rich water" Journal of Hazardous Materials, Elsevier, Asterdam, NL, vol. 157, No. 2-3, Jan. 16, 2008, pp. 553-563.

Wang, Pan et al. "Isolation and immobilization of new aerobic denitrifying bacteria", International Biodeterioration & Biodegradation, vol. 76, Jul. 9, 2012, pp. 12-17.

(56) References Cited

OTHER PUBLICATIONS

Huang, Ting-Lin et al. "Nitrogen Removal from Micro-Polluted Reservior Water by Indigenous Aerobic Denitrifiers" International Journal of Molecular Sciences, vol. 16, No. 4, Apr. 10, 2015, pp. 8008-8026.

Gorsuch, J. P. et al. "Aerobic Nitrification and Denitrification among Heterotrophic Bacterial Isolates from a Commercial Water Treatment Product (Biowish™ Aqua)", Dec. 2015.

Encyclopedia of Food and Color Additives. Dextrose monohydrate. Soy lecithin. CRC Press (publisher). First edition. 1997. CRC Press, Inc. Ed.: George A. Burdock, Ph.D., Boca Raton. FL.pp. 797, 1553-1554.

Sargent, M.G. Jul. 1975. Control of cell length in Bacillus subtilis. Journal of Bacteriology 123(1): 7-19. Specif. p. 10.

Baetge et al., "Complete nucleotide and deduced amino acid sequence of bovine phenylethanolamine N-methyltransferase: Partial amino acid homology with rat tyrosine hydroxylase", *Proc. Natl. Acad. Sci. USA*, 83: 5454-5458 (1986).

\* cited by examiner

MICROBIAL COMPOSITIONS AND METHODS FOR DENITRIFICATION AT HIGH DISSOLVED OXYGEN LEVELS

RELATED APPLICATIONS

This application claims priority to and benefit of U.S. Provisional Application No. 62/157,327, filed on May 5, 2015, the contents of which are hereby incorporated by reference in their entireties.

INCORPORATION-BY-REFERENCE OF SEQUENCE LISTING

The contents of the text file named "BIOW-014-001WO-Sequence Listing.txt", which was created on Apr. 29, 2016 and is 14.5 KB in size, are hereby incorporated by reference in their entireties.

FIELD OF THE INVENTION

The present invention relates to water treatment compositions containing microorganisms and methods of using the compositions to remove nitrate levels in water.

BACKGROUND OF THE INVENTION

The biological removal of inorganic nitrogenous compounds, such as ammonium ($NH_4^+$) and nitrate ($NO_3$) from aquatic systems has long been a topic of interest for wastewater engineers and other water treatment professionals. These compounds contribute to eutrophication and are toxic to many aquatic organisms; therefore their presence in treated wastewater and in clean water systems, such as ponds, lakes, and reservoirs, is undesirable (Shannon et al, 2008). In the past, combinations of autotrophic nitrifying and denitrifying bacteria (which convert $NH_4^+$ to $N_2$, with $NO_3^-$ as an intermediate) were believed to be the only method for effecting such remediation. However, the discovery of novel metabolic pathways among several bacterial taxa during the latter part of the 20th century forced a reevaluation of this paradigm (Schmidt et al, 1987).

Nitrifying and denitrifying bacteria are an integral part of the planet's Nitrogen Cycle. Three main types of bacteria catalyze the conversions shown above. Ammonia oxidizing bacteria (AOBs) are aerobic chemolithoautotrophs belonging to the phylum Proteobacteria, which contains species such as *Nitrosomonas, Nitrosococcus*, and *Nitrospira* (Koops and Pommererening-Röser, 2001). These convert ammonia ($NH_4^+$) into hydroxylamine ($NH_2OH$) through the action of ammonia monooxygenase (Equation 1). Hydroxylamine is then converted to nitrite ($NO_2^-$) by hydroxylamine oxidoreductase (Equation 2). Doubling time for these organisms ranges from 8-24 hours depending on nutrient availability (Hommes et al, 2003).

$$NH_3+O_2+2H^++2e^- \rightarrow NH_2OH+H_2O \quad (1)$$

$$NH_2OH+H_2O \rightarrow NO_2^-+5H^++4e^- \quad (2)$$

A second group of Proteobacteria, called nitrite oxidizing bacteria (NOBs), then converts nitrite into nitrate (Equation 3) with the enzyme nitrite oxidoreductase (Prosser, 1989). These are also *aerobic chemolithoautotrophs*, among the most common being members of the genus *Nitrobacter*. These organisms have a maximum doubling time of 20 hours (Tramper and Grootjen, 1986).

$$NO_2^-+H_2O \rightarrow NO_3^-+2H^++2e^- \quad (3)$$

Nitrate is then converted into $N_2$ in a process called denitrification (Equation 4), which was long believed to be limited to bacteria such as *Thiosphaera, Paracoccus* and *Pseudomonas* and to eukaryotes such as algae and fungi (Shapleigh, 2006). However, recent studies have found that members of the genus *Bacillus* (heterotrophic organisms of the phylum Firmicutes) can perform denitrification as well (Verbaendert, 2011). During denitrification, nitrate is substituted for oxygen as a terminal electron acceptor; therefore, because oxygen is an energetically preferable electron acceptor, denitrification generally occurs in anoxic environments. Nitrate is converted to nitrite before being ultimately converted to $N_2$.

$$2NO_3^-+10e^-+12H^+ \rightarrow N_2+6H_2O \quad (4)$$

The discovery of anaerobic ammonia oxidizers, collectively referred to as "anammox" bacteria, of the phylum Planctomycetes and belonging to genera such as *Brocadia* provided a new method for remediating inorganic nitrogenous compounds in wastewater (Strous et al, 1999). Organisms such as *B. anammoxidans* carry out denitrification of nitrite, using ammonia as an electron donor, with $H_2O$ and $N_2$ as end products (Equation 5). Though their metabolism of ammonia was seen as quite novel, these bacteria are notoriously slow growing (doubling time approaches 11 days) and their anaerobic ammonia metabolism is completely, albeit reversibly, inhibited by oxygen at concentrations as low as 2 µM (Jetten et al, 2001).

$$NH_4^++NO_2^- \rightarrow N_2+2H_2O \quad (5)$$

Practical applications of these bacterial systems are numerous. In Partial Nitrification reactors (Hellinga et al, 1998), AOBs are utilized to convert ammonia into nitrite. Rather than allowing the nitrite to be converted to nitrate by NOBs (which must be inhibited in these systems through temperature and pH controls) the nitrite enriched wastewater is instead added to a denitrification reactor and converted to $N_2$ by denitrifying bacteria. This allows the denitrifying bacteria to conserve energy, as they do not need to derive their $NO_2^-$ from $NO_3^-$. The Partial Denitrification process can also be coupled with an anammox reactor in a process known as SHARON (single reactor system for high activity ammonium removal over nitrite), which allows the anammox Planctomycetes to utilize both $NH_4^+$ and $NO_2^-$ to effect denitrification (Hellinga et al, 1998). Canon (completely autotrophic nitrogen removal over nitrite) reactors employ aerobic nitrifying bacteria from the phylum Proteobacteria for nitrification and anaerobic Planctomycetes for denitrification (Third et al, 2001). Aerobic AOBs oxidize $NH_4^+$ to $NO_2^-$ while consuming oxygen, which creates an anoxic environment in which anammox bacteria can thrive. In addition to being hindered by the extended startup times of Planctomycetes, this system is prone to a buildup of $NO_2^-$ in the presence of excess $O_2$. Finally, $NO_x$ processes (Bock et al 1996) involve augmenting cultures of aerobic Proteobacteria such as *Nitrosomonas* with nitrogen oxides, which stimulates the bacteria to perform nitrification and denitrification concurrently (Bock et al, 1996).

Heterotrophic nitrification involves the conversion of $NH_4^+$ to $NO_2^-$ by heterotrophic bacteria which, unlike the autotrophic *Nitrosomonas*, rely on organic compounds as a carbon and energy source (Schreiber, 2009). Though known to take place among some bacteria such as *Thiosphaera pantotropha* and some species in the genus *Pseudomonas*, rates of nitrification and denitrification were observed to be slower among heterotrophs (Schmidt et al, 2003). Therefore, autotrophs were viewed as superior organisms for remediating inorganic nitrogenous compounds in wastewater. However, Kim et al (2005) observed aerobic nitrification and denitrification among several strains of *Bacillus* (phylum Firmicutes) at higher rates than had been observed previously among heterotrophs. Nitrogen balance revealed that some ammonia nitrogen had been completely lost from the system, presumably as $N_2$. This suggested a less complicated metabolic pathway among *Bacillus* than exists among Proteobacteria and Planctomycetes, as well as a potential alternative to the current nitrification and denitrification systems dominated by autotrophs.

SUMMARY OF THE INVENTION

In various aspects the invention provides compositions containing a mixture of microorganisms selected on the basis of their ability to degrade nitrate in a simulated waste water environment at high dissolved oxygen (DO) levels. Individual bacteria comprising the mixture are selected based on their ability to degrade nitrate at a rate of at least 0.005 mM/hr in a simulated waste water environment when the DO levels are at or above 3 ppm.

Microbes are selected based on their ability to degrade nitrate under high DO levels in a "simulated" waste water environment. The "simulated" waste water is created by adding a carbon source (in the form of dextrose) and nitrogen source (in the form of ammonia) along with other nutrients known to facilitate microbial growth to deionized water pH adjusted to 7.0. The C:N ratio in the media ranges from 1:1 to 10:1. Nitrate, in the form of sodium nitrate, is added to this "simulated" system and the concentration monitored over time when microbes are added. The rate of nitrate degradation is estimated from the pseudo-first order rate based on a regression analysis of the nitrate concentration versus time data in $\ln(C_t/C_0)/t$ form. Any microbe with a denitrification rate above about 0.005 mM/hr, at DO levels above about 3 ppm, in this assay is acceptable for use.

In various aspects the invention provides compositions and methods for degrading nitrate in aqueous systems. The compositions contain a mixture of *Bacillus* organisms or a mixture of *Bacillus* and *Lactobacillus* organisms. The mixture of *Bacillus* organisms can include *Bacillus subtilis, Bacillus amyloliquefaciens, Bacillus licheniformis* and *Bacillus pumilus*. The mixture of *Lactobacillus* organisms can include *Pediococcus acidilactici, Pediococcus pentosaceus*, and *Lactobacillus plantarum*. Preferably, the composition includes a mixture of *Bacillus* organisms and a mixture of *Lactobacillus* organisms. In some embodiments the compositions may contain *Bacillus subtilis, Bacillus licheniformis, Bacillus pumilus, Bacillus amyloliquefaciens, Bacillus mojavensis, Pediococcus acidilactici, Pediococcus pentosaceus*, and *Lactobacillus plantarum*. In other embodiments the composition contains *Bacillus subtilis, Bacillus liceniformis*, and *Bacillus pumilus*. The *Bacillus subtilis* can include *Bacillus subtilis* 34KLB and/or *Bacillus s subtilis* subsp. *Mojavensis*. Each of the organisms is individually aerobically (*Bacillus*) or anaerobically (*Lactobacillus*) fermented, harvested, dried, and ground to produce a powder having a mean particle size of about 200 microns, with greater than 60% of the mixture in the size range between 100-800 microns. In some embodiments, the ratio of the *Bacillus* to *Lactobacillus* is between 1:10 to 10:1. Preferably, the ratio of the *Bacillus* to *Lactobacillus* is about 1:3.3. In some embodiments, the ratio of *Pediococcus acidilactici, Pediococcus pentosaceus*, and *Lactobacillus plantarum* is 1:1:1 by weight.

In some aspects the composition has a moisture content of less than about 5% and a final bacterial concentration of about $10^5$ to $10^{11}$ colony forming units (CFU) per gram of the composition.

In various aspects the compositions further contain an inert carrier such as dextrose monohydrate. Preferably, the inert carrier is at a concentration of about 75 to about 95% (w/w).

In a preferred embodiment, the composition comprises about 87% by weight of dextrose, about 1% by weight of *Bacillus* Mix #1, about 1% by weight of *Bacillus* Mix #2, about 1% by weight of *Bacillus* Mix #3 and about 10% by weight of *Lactobacillus* Mix #1.

Also included in the invention are methods for treating aqueous systems by contacting said systems with a composition containing the microbial mixtures of the invention. The aqueous system is for example, municipal sewage, residential or commercial septic, industrial wastewater, livestock waste water lagoons, aquaculture ponds, waste water from fruit and vegetable processing, waste water from brewery and distilling, swimming pools, or spas. The method results in decreased nitrate concentrations even at high DO levels.

Also provided by the invention are methods of manufacturing the compositions of the invention. Microbial mixtures are manufactured by individually fermenting each organism under conditions optimal for its growth; harvesting each microbe, drying the harvested organisms; grinding the dried organisms to produce a powder, then combining each of the dried, ground powders to produce the final preferred compositions. The final microbial mixture has a moisture content of less than about 5%; and a final bacterial concentration of between about $10^5$ to $10^{11}$ CFU/gram.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions will control. In addition, the materials, methods, and examples described herein are illustrative only and are not intended to be limiting.

Other features and advantages of the invention will be apparent from and encompassed by the following detailed description, examples, and claims.

DETAILED DESCRIPTION OF THE INVENTION

Figure 1:
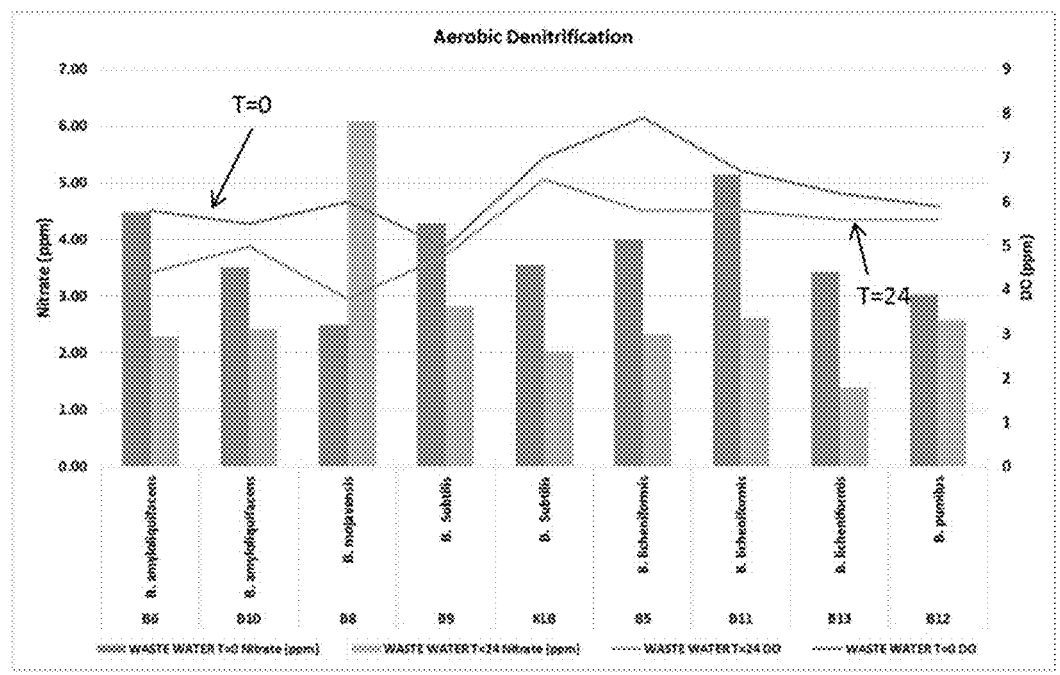
FIG. 1 is a bar graph demonstrating denitrification in waste water samples. For each bar pair, the left bar shows nitrate levels at T=0 and the right bar shows T=24 hours. The lines illustrate DO levels at T=0 (blue) and T=24 (grey) hours. The data show significant denitrification for all *Bacillus* strains except the *B. mojavensis* without appreciable loss in DO.

The invention provides microbial compositions and methods for removing nitrate from aqueous systems at dissolved oxygen (DO) levels above about 3 ppm. The microbes used in the product according to the present invention maybe any conventional psycrophilic, mesophilic or thermophilic bacteria. More preferred are bacteria selected from the Lactobacillaceae and Bacillaceae families. Most preferred are the bacteria selected from the genera *Bacillus* and *Lactobacillus*.

Bacteria from the genera *Bacillus* and *Lactobacillus* offer a number of potential advantages over members of the phyla Proteobacteria and Planctomycetes. The ability of *Bacillus* to form endospores provides for hardier suspensions that can remain viable under a wider range of environmental conditions than preparations of vegetative cells. Additionally, while Proteobacteria such as *Nitrosomonas* and *Nitrobacter* have doubling times of 8-24 hours and anammox species have doubling times in excess of seven days, members of the genera *Bacillus* and *Lactobacillus* have doubling times as low as 40 minutes under optimal conditions (Hageman et al, 1984). Thus, these bacteria may offer several economic advantages over their more common wastewater treatment counterparts.

The microbes in the compositions are chosen based on their ability to degrade nitrate in a "simulated" waste water environment at DO levels above about 3 ppm. The "simulated" waste water is comprised of an aqueous mix of dextrose, ammonia, soy peptone, casein digest buffered to about pH 7.0. The C:N ratio in this simulated system ranges from 1:1 to 10:1. Microbes having a rate of nitrate degradation greater than about 0.005 mM/hr, where the rate is determined from the pseudo-first order linear fit of the $\ln(C_t/C_0)/t$ data, are preferred. The microbes in compositions according to the present invention can have a rate of nitrate degradation greater than about 0.01 mM/hr, greater than about 0.02 mM/hr or greater than about 0.1 mM/hr. The microbes in compositions according to the present invention can have a rate of nitrate degradation in the range of about 0.005 mM/hr to about 0.5 mM/hr, about 0.005 mM/hr to about 0.2 mM/hr, or about 0.01 mM/hr to about 0.1 mM/hr.

The terms "microbial", "bacteria" or "microbes" as used herein, refer to microorganisms that confer a benefit. The microbes according to the invention may be viable or non-viable. The non-viable microbes are metabolically-active. By "metabolically-active" is meant that they exhibit at least some residual enzyme or secondary metabolite activity characteristic to that type of microbe.

By the term "non-viable" as used herein is meant a population of bacteria that is not capable of replicating under any known conditions. However, it is to be understood that due to normal biological variations in a population, a small percentage of the population (i.e. 5% or less) may still be viable and thus capable of replication under suitable growing conditions in a population which is otherwise defined as non-viable.

By the term "viable bacteria" as used herein is meant a population of bacteria that is capable of replicating under suitable conditions under which replication is possible. A population of bacteria that does not fulfill the definition of "non-viable" (as given above) is considered to be "viable."

"Wastewater," as used herein, is directed to domestic sewage from dwellings, business buildings, institutions, and farms, which contain ground water, surface water, and/or storm water. Wastewater also includes water produced during the processing or washing of products such as fruit and vegetables.

"Aqueous systems," as used herein, refers to "wastewater" as well as swimming pools, spas, and aquaculture ponds.

"Treating" as used herein, means inoculating "Aqueous systems" with microbes designed to enhance efficient degradation of nitrate and DO levels above about 3 ppm.

As used herein, the term "about" in conjunction with a numeral refers to the numeral and a deviation thereof in the range of +10% of the numeral. For example, the phrase "about 100" refers to a range of 90 to 110.

A preferred composition according to the invention includes about 85% to 95% by weight of dextrose and the remainder by weight of a microbial mixture. Preferably, the microbial mixture includes a *Bacillus* mixture and a *Lactobacillus* mixture. The dextrose can be dextrose monohydrate, anhydrous dextrose or a combination thereof.

In some aspects, the microbial compositions contain a mixture of *Bacillus*.

Preferred *Bacillus* includes *B. subtilis*, *B. amyloliquefaciens*, *B. licheniformis*, *B. pumilus*, *B. mojavensis*, *B. coagulans*, *B. megaterium*, and *Paenibacillus polymyxa*. Among the preferred *Bacillus* species *Bacillus subtilis*, *Bacillus licheniformis*, *Bacillus amyloliquefaciens* and *Bacillus pumilus* are most preferred. The *Bacillus subtilis* can include Mojavensis. The *Bacillus subtilis* can include *Bacillus subtilis* 34KLB.

In other aspects the microbial compositions contain a mix of *Bacillus* and *Lactobacillus* bacteria. Preferred *Lactobacillus* species include *Pediococcus acidilactici*, *Pediococcus pentosaceus*, and *Lactobacillus plantarum*. In such compositions, the weight ratio of *Bacillus* to *Lactobacillus* ranges from 1:10 to 10:1 (e.g., 1:10, 1:9, 1:8, 1:7, 1:6, 1:5, 1:4, 1:3, 1:2, 1:1, 2:1, 3:1, 4:1, 5:1, 6:1, 7:1, 8:1, 9:1 or 10:1). Preferably, the weight ratio of *Bacillus* to *Lactobacillus* is about 1:3.3. Other preferred compositions include those wherein the *Lactobacillus* are mixed together in a ratio of 1:1:1.

The amino acid sequence of *Bacillus subtilis* 34KLB is shown below:

*Bacillus subtilis* strain 34KLB
(SEQ ID NO: 1)
AGCTCGGATCCACTAGTAACGGCCGCCAGTGTGCTGGAATTCGCCCTTAG

AAAGGAGGTGATCCAGCCGCACCTTCCGATACGGCTACCTTGTTACGACT

TCACCCCAATCATCTGTCCCACCTTCGGCGGCTGGCTCCATAAAGGTTAC

CTCACCGACTTCGGGTGTTACAAACTCTCGTGGTGTGACGGGCGGTGTGT

ACAAGGCCCGGGAACGTATTCACCGCGGCATGCTGATCCGCGATTACTAG

CGATTCCAGCTTCACGCAGTCGAGTTGCAGACTGCGATCCGAACTGAGAA

CAGATTTGTGRGATTGGCTTAACCTCGCGGTTTCGCTGCCCTTTGTTCTG

TCCATTGTAGCACGTGTGTAGCCCAGGTCATAAGGGGCATGATGATTTGA

CGTCATCCCCACCTTCCTCCGGTTTGTCACCGGCAGTCACCTTAGAGTGC

CCAACTGAATGCTGGCAACTAAGATCAAGGGTTGCGCTCGTTGCGGGACT

TAACCCAACATCTCACGACACGAGCTGACGACAACCATGCACCACCTGTC

-continued

```
ACTCTGCCCCCGAAGGGGACGTCCTATCTCTAGGATTGTCAGAGGATGTC

AAGACCTGGTAAGGTTCTTCGCGTTGCTTCGAATTAAACCACATGCTCCA

CCGCTTGTGCGGGCCCCCGTCAATTCCTTTGAGTTTCAGTCTTGCGACCG

TACTCCCCAGGCGGAGTGCTTAATGCGTTAGCTGCAGCACTAAAGGGCG

GAAACCCCTAACACTTAGCACTCATCGTTTACGGCGTGGACTACCAGGG

TATCTAATCCTGTTCGCTCCCCACGCTTTCGCTCCTCAGCGTCAGTTACA

GACCAGAGAGTCGCCTTCGCCACTGGTGTTCCTCCACATCTCTACGCATT

TCACCGCTACACGTGGAATTCCACTCTCCTCTTCTGCACTCAAGTTCCCC

AGTTTCCAATGACCCTCCCCGGTTGAGCCGGGGCTTTCACATCAGACTT

AAGAAACCGCCTGCGAGCCCTTTACGCCCAATAAtTCCGGACAACGCTTG

CCACCTACGTATTACCGCGGCTGCTGGCACGTAGTTAGCCGTGGCTTTCT

GGTTAGGTACCGTCAAGGTGCCGCCCTATTTGAACGGCACTTGTTCTTCC

CTAACAACAGAGCTTTACGATCCGAAAACCTTCATCACTCACGCGGCGTT

GCTCCGTCAGACTTTCGTCCATTGCGGAAGATTCCCTACTGCTGCCTCCC

GTAGGAGTCTGGGCCGTGTCTCAGTCCCAGTGTGGCCGATCACCCTCTCA

GGTCGGCTACGCATCGTCGCCTTGGTGAGCCGTTACCTCACCAACTAGCT

AATGCGCCGCGGGTCCATCTGTAAGTGGTAGCCGAAGCCACCTTTTATGT

CTGAACCATGCGGTTCAGACAACCATCCGGTATTAGCCCCGGTTTCCCGG

AGTTATCCCAGTCTTACAGGCAGGTTACCCACGTGTTACTCACCCGTCCG

CCGCTAACATCAGGGAGCAAGCTCCCATCTGTCCGCTCGACTTGCATGTA

TTAGGCACGCCGCCAGCGTTCGTCCTGAGCCATGAACAAACTCTAAGGGC

GAATTCTGCAGATATCCATCACACTGGCGGCCGCTCGAGCATGCATCTAG

AGGGCCCAATCGCCCTAT
```

The *Bacillus* mixture includes about 10-50% *Bacillus subtilis* by weight (e.g., about 10%, about 15%, about 20%, about 25%, about 30%, about 35%, about 40%, about 45%, or about 50% by weight). The *Bacillus* mixture includes about 10-50% *Bacillus amyloliquefaciens* by weight (e.g., about 10%, about 15%, about 20%, about 25%, about 30%, about 35%, about 40%, about 45%, or about 50% by weight). The *Bacillus* mixture includes about 10-50% *Bacillus licheniformis* by weight (e.g., about 10%, about 15%, about 20%, about 25%, about 30%, about 35%, about 40%, about 45%, or about 50% by weight). The *Bacillus* mixture includes about 10-50% *Bacillus pumilus* by weight (e.g., about 10%, about 15%, about 20%, about 25%, about 30%, about 35%, about 40%, about 45%, or about 50% by weight).

The *Lactobacillus* mixture includes about 10-50% *Pediococcus acidilactici* by weight (e.g., about 10%, about 15%, about 20%, about 25%, about 30%, about 35%, about 40%, about 45%, or about 50% by weight). Preferably, the mixture includes about 30% to 35% *Pediococcus acidilactici* by weight. The *Lactobacillus* mixture includes about 10-50% *Pediococcus pentosaceus* by weight (e.g., about 10%, about 15%, about 20%, about 25%, about 30%, about 35%, about 40%, about 45%, or about 50% by weight). Preferably, the mixture includes about 30% to 35% *Pediococcus pentosaceus* by weight. The *Lactobacillus* mixture includes about 10-50% *Lactobacillus plantarum* by weight (e.g., about 10%, about 15%, about 20%, about 25%, about 30%, about 35%, about 40%, about 45%, or about 50% by weight). Preferably, the mixture includes about 30% to 35% *Lactobacillus plantarum* by weight. More preferably the *Lactobacillus* is present in the mixture in equal amounts by weight. Most preferably the mixtures contains about 33.3% *Pediococcus acidilactici* by weight, 33.3% *Pediococcus pentosaceus* by weight and about 33.3% *Lactobacillus plantarum* by weight.

A first preferred *Bacillus* mixture includes 10% by weight *Bacillus licheniformis*, 30% by weight *Bacillus pumilus*, 30% by weight *Bacillus amyloliquefaciens* and 30% by weight *Bacillus subtilis* (referred to herein as *Bacillus* Mix #1). Preferably, the *Bacillus subtilis* in *Bacillus* Mix #1 is *Bacillus subtilis*; subsp. *Mojavenisi*.

A second preferred *Bacillus* mixture includes 20% by weight *Bacillus licheniformis*, 30% by weight *Bacillus pumilus*, 30% by weight *Bacillus amyloliquefaciens* and 20% by weight *Bacillus subtilis* (referred to herein as *Bacillus* Mix #2).

A third preferred *Bacillus* mixture includes *Bacillus subtilis* 34 KLB (referred to herein as *Bacillus* Mix #3).

A preferred *Lactobacillus* mixture includes equal weights of *Pediococcus acidilactici*, *Pediococcus pentosaceus* and *Lactobacillus plantarum* (referred to herein as *Lactobacillus* Mix #1).

A preferred composition according to the invention includes at least about 85% by weight of dextrose, about 0.1 to 5% by weight of *Bacillus* Mix#1, about 0.1 to 5% by weight of *Bacillus* Mix#2, about 0.1 to 5% *Bacillus* Mix #3 and about 1 to 15% by weight of *Lactobacillus* Mix #1. Preferably, the composition according to the invention includes about 0.1 to 4%, 0.1 to 3%, 0.1 to 2% or 0.5 to 1.5% by weight of *Bacillus* Mix#1, about 0.1 to 4%, 0.1 to 3%, 0.1 to 2% or 0.5 to 1.5% by weight of *Bacillus* Mix#2, 0.1 to 4%, 0.1 to 3%, 0.1 to 2% or 0.5 to 1.5% by weight of *Bacillus* Mix#3, and about 1 to 14%, 1 to 13%, 1 to 12%, 5 to 15%, 6 to 15%, 7 to 15% or 8 to 12% by weight of *Lactobacillus* Mix #1.

Another preferred composition according to the invention includes about 85% by weight of dextrose, about 1% by weight of *Bacillus* Mix#1, about 1% by weight of *Bacillus* Mix#2, about 1% *Bacillus* Mix #3 and about 10% by weight of *Lactobacillus* Mix #1.

The levels of bacteria to be used according to the present invention will depend upon the types thereof. It is preferred that the product anticipated by the present invention contains bacteria in an amount between about $10^5$ and $10^{11}$ colony forming units (CFU) per gram.

The bacteria according to the invention may be produced using any standard fermentation process known in the art. For example, solid substrate or submerged liquid fermentation. The fermented cultures can be mixed cultures or single isolates.

In some embodiments the bacteria are aerobically fermented. For those bacteria capable of forming spores, the fermentation process includes a "shock" step to drive the bacteria into spore form. Any "shock" method known in the art is suitable for this process. For example, the fermentation may be heat shocked to achieve sporulation.

In some embodiments the bacteria are anaerobically fermented in the presence of carbohydrates. Suitable carbohydrates include inulin, fructo-oligosaccharide, and gluco-oligosaccharides.

The bacterial compositions are in powdered, dried form. Alternatively, the bacterial compositions are in liquid form.

After fermentation the bacteria are harvested by any known methods in the art. For example, the bacteria are harvested by filtration or centrifugation.

The bacteria are dried by any method known in the art. For example, the bacteria are air dried, or dried by freezing in liquid nitrogen followed by lyophilization.

The compositions according to the invention have been dried to moisture content less than 20%, 15%, 10%, 9%, 8%, 7%, 6%, 5%, 4%, 3%, 2%, or 1% by weight. Preferably, the composition according to the invention has been dried to moisture content less than 5% by weight.

In some embodiments the dried powder is ground to decrease the particle size. The bacteria are ground by conical grinding at a temperature less than 10° C., 9° C., 8° C., 7° C., 6° C., 5° C., 4° C., 3° C., 1° C., 0° C., or less. Preferably, the temperature for grinding is less than about 4° C.

The resulting powdered product has a particle size less than 1500, 1400, 1300, 1200, 1100, 1000, 900, 800, 700, 600, 500, 400, 300, 200, or 100 microns. Preferably, the freeze dried powder is ground to decrease the particle size such that the particle size is less than about 800 microns. Most preferred are particle sizes less than about 400 microns. In most preferred embodiments, the dried powder has a mean particle size of 200 microns, with 60% of the mixture in the size range between 100-800 microns. In various embodiments the freeze dried powder is homogenized.

In various embodiments the bacteria compositions are mixed with an inert carrier such as dextrose monohydrate. The inert carrier is at a concentration of at least 60%, 70%, 75%, 80%, 85%, 90%, 95% or more by weight. Preferably, the inert carrier is at a concentration of between about 75% and 95% (wt/wt). Preferably, the inert carrier is dextrose monohydrate. More preferably, the dextrose monohydrate is at a concentration of about between 80-95% (w/w), e.g., about between 80-90% (w/w).

Further, if desired, the bacterial compositions may be encapsulated to further increase the probability of survival; for example, in a sugar matrix, fat matrix, or polysaccharide matrix.

The bacterial compositions of the invention are used to treat commercial, municipal, industrial, and residential wastewater, livestock ponds, aquaculture ponds, swimming pools, spas, and aquariums.

One or more embodiments relate generally to treatment of aqueous systems. An aqueous system may contain wastewater from a community, industrial, or residential source during typical operation. For example, the wastewater may be delivered from a municipal or other large-scale sewage system. Alternatively, the wastewater may be generated, for example, during wash down of livestock pens, or by food processing or pulp and paper plants.

Aqueous systems may generally be any water compartment containing high nitrate levels with dissolved oxygen levels above about 3 ppm, above about 5 ppm, above about 10 ppm, above about 20 ppm, above about 50 ppm or about 3-50 ppm (e.g., 3-40 ppm, 3-30 ppm or 3-20 ppm).

The compositions are typically delivered to the aqueous system as a solid. However, in some applications it may be preferred to pre-dissolve the composition in water and add this premix to the final aqueous system. In other applications, the compositions may be incorporated onto a solid support (e.g., a filter) through which the water to be denitrified is passed.

The compositions of the invention are manufactured by any method suitable for production of bacterial compositions. Preferably, mixtures containing either multiple Bacillus species or mixtures of Bacillus and Lactobacillus, are manufactured by individually fermenting each organism under conditions ideal for growth of that specific organism; harvesting each organism; drying the harvested organisms; grinding the dried organisms to produce a powder; then, combining each individual organism into the final mix. For compositions comprising mixtures of Bacillus species only, the individual Bacillus organisms are mixed together at equal levels. For compositions comprising mixtures of Bacillus and Lactobacillus the ratio of Bacillus to Lactobacillus ranges from 1:10 to 10:1. The Bacillus organisms of the invention include Bacillus subtilis, Bacillus amyloliquefaciens, Bacillus licheniformis, Bacillus pumilus, Bacillus megaterium, Bacillus coagulans, and, Paenibacillus polymyxa. The Lactobacillus organisms of the invention include Pediococcus acidilactici, Pediococcus pentosaceus, and Lactobacillus plantarum. The microbial compositions have a moisture content of less than about 5%, a mean particle size of about 200 microns, and a final bacterial concentration of between about $10^5$ to $10^{11}$ CFU/gram of the composition.

A better understanding of the present invention may be given with the following examples which are set forth to illustrate, but are not to be construed to limit, the present invention.

EXAMPLES

Example 1: Preparation of the Microbial Species

The microbes of the present invention are grown using standard deep tank submerged fermentation processes known in the art.

Bacillus Species

Individual starter cultures of Bacillus subtilis, Bacillus amyloliquefaciens, Bacillus licheniformis, Bacillus pumilus, and Bacillus mojavensis are grown according to the following general protocol: 2 grams Nutrient Broth, 2 grams AmberFerm (Yeast Extract), and 4 grams Maltodextrin are added to a 250 mL Erlenmeyer flask. 100 mL distilled, deionized water is added and the flask is stirred until all dry ingredients are dissolved. The flask is covered and placed for 30 minutes in an autoclave operating at 121° C. and 15 psi. After cooling, the flask is inoculated with 1 mL of one of the pure microbial strains. The flask is sealed and placed on an orbital shaker at 30° C. Cultures are allowed to grow for 3-5 days. This process is repeated for each of the bacillus microbes in the mixture. In this way starter cultures of Bacillus subtilis, Bacillus amyloliquefaciens, Bacillus licheniformis, Bacillus pumilus, and Bacillus mojavensis are prepared.

Larger cultures are prepared by adding 18 grams Nutrient Broth, 18 grams AmberFerm, and 36 grams Maltodextrin to 1 liter flasks with 900 mL distilled, deionized water. The flasks are sealed and sterilized as above. After cooling, 100 mL of the microbial media from the 250 mL Erlenmeyer flasks are added. The 1 liter flasks are sealed, placed on an orbital shaker, and allowed to grow out for another 3-5 days at 30° C.

In the final grow-out phase before introduction to the fermenter, the cultures from the 1 liter flasks are transferred under sterile conditions to pre-sterilized full-scale fermentation tanks and fermentation is continued, at the pH and temperature optimum of each organism, with aeration until stationary phase is achieved. Once bacterial growth has stabilized at about $10^{11}$ CFU/mL the fermenter is heat shocked to encourage spore formation. The individual fermenters are then emptied, filtered, and centrifuged to obtain the bacterial spores which are dried under vacuum until moisture drops below 5% then ground to a particle size of about 200 microns. In this way, individual dried cultures of *Bacillus subtilis, Bacillus amyloliquefaciens, Bacillus licheniformis, Bacillus pumilus*, and *Bacillus mojavensis* spores are prepared. The final microbial count of the individual dried samples ranges from $10^9$ to $10^{11}$ CFU/g.

*Lactobacillus* Species

Individual, purified isolates of *Pediococcus acidilactici, Pediococcus pentosaceus*, and *Lactobacillus plantarum* are grown-up in separate fermenters using standard anaerobic submerged fermentation protocols at the pH and temperature optimum for each species:

| Microbe | pH Optimum | Temperature Optimum |
|---|---|---|
| *Pediococcus acidilactici* | 5.5 | 37° C. |
| *Pediococcus pentosaceus* | 5.5 | 37° C. |
| *Lactobacillus plantarum* | 6.0 | 35° C. |

After fermentation the individual cultures are filtered, centrifuged, freeze dried to a moisture level less than about 5%, then ground to a particle size of about 200 microns. In this way, individual dried cultures of *Pediococcus acidilactici, Pediococcus pentosaceus*, and *Lactobacillus plantarum* are prepared. The final microbial count of the individual dried samples ranges from $10^8$ to $10^{10}$ CFU/g.

Example 2: Preparation of Simulated Waste Water

Several liters of simulated waste water having the following composition were prepared and stored in a sterilized container:

| Ingredient | Amount (grams/L) |
|---|---|
| Dextrose | 0.282 |
| Casein Digest | 0.282 |
| Soy Peptone | 0.150 |
| Ammonia | 0.012 |
| pH | 7.0 |

Samples were removed under sterile conditions as needed for the denitrification experiments.

Example 3: Denitrification Experiments in Simulated Waste Water 150 mL of simulated waste water from Example 2 was added to sterile, 500 mL Erlenmeyer flasks along with sodium nitrate (≥99%, Sigma Aldrich) to achieve a final nitrate concentration of 25 mg/L. Inoculums of each bacterial isolate from Example 1 were added to the reactor flasks from which a 15 mL sample (T=0) was immediately, aseptically removed using a sterile serological pipette and stored inside a sterile, screw-capped 15 mL centrifuge tube. Reactor flasks were placed inside an incubator/shaker set 40° C. (for the *Bacillus* species) or 35° C. (for *Lactobacillus* and *Pediococcus*). Flasks were periodically removed for sampling at hours 2, 3, 4, 5, 6, and 24. Sample tubes were centrifuged at 6,000 rpm for 10 minutes to remove suspended cells, which may interfere with spectrophotometric analysis. Following centrifugation, 5 mL aliquots were removed from the tube using an autopipettor and dispensed into 20 mL scintillation vials for colorimetric analysis.

Nitrate concentrations were determined colorimetrically using a commercially available test kit (MARS Fishcare). Reactions were performed as indicated by the test kit. 5-7 minutes were allowed for samples to fully react before measuring absorbance. Nitrate absorbance was measured at 546 nm on a DU-520 spectrophotometer (Beckman-Coulter). A standard curve was created before the test samples were measured. The linear best fit of the absorbance (Y-value) vs. added nitrate concentration (X-value) followed the equation Y=1896.7X+0.0377 with an $r^2$ value of 0.999.

A commercial dissolved oxygen test kit (LaMotte) was used as directed to titrate dissolved oxygen within the reactor flasks. Samples were not kept air-tight during reaction flask incubation.

Four selected species of *Bacillus* (*B. pumilus, B. subtilis* (2 strains), *B. licheniformis*, and *B. mojavensis*) and all three *Lactobacillus* from Example 1 were screened for aerobic denitrification. Results are summarized below:

| | Simulated Waste Water | | |
|---|---|---|---|
| Isolate | Rate (mM hr$^{-1}$) | DO (ppm) T = 0 | DO (ppm) T = 24 |
| *B. subtilis* (strain 1) | −0.005 | 5.0 | 4.5 |
| *B. subtilis* (strain 2) | −0.009 | 6.1 | 4.8 |
| *B. mojavensis* | 0.001 | 6.1 | 4.9 |
| *B. pumilus* | −0.144 | 6.3 | 4.9 |
| *B. licheniformis* | −0.132 | 7.1 | 5.8 |
| *P. acidilactici* | −0.032 | 5.6 | 3.4 |
| *P. pentosaceus* | −0.022 | 6.2 | 5.1 |
| *L. plantarum* | −0.001 | 4.3 | 3.2 |

Rates of denitrification are estimates of the pseudo-first order rate based on a regression analysis of the data in $\ln(C_t/C_0)/t$ form where $C_t$ is the nitrate concentration at any given time (t) and $C_0$ is the initial nitrate concentration. Negative values indicate degradation of nitrate over time. Positive values indicate nitrate production over time.

Example 4: Denitrification Experiments in Waste Water Extract

Several gallons of filtered, untreated wastewater were collected from the Sycamore Creek Wastewater Treatment Plant (Cincinnati, Ohio USA) in a disinfected, capped plastic carboy. The wastewater was centrifuged at 6,000 rpm for ten minutes to remove visible Biosolids then filtered through a 0.22 micron cellulose acetate membrane filter. 150 mL aliquots were dispensed into 500 mL Erlenmeyer flasks along with sufficient sodium nitrate to achieve a final nitrate concentration of 25 mg/L. The flasks were then capped with foil and autoclaved at 121° C., 15 psi for 15 minutes in order to remove any potential pathogenic enteric bacteria. Flasks were sealed and stored at 4° C. until needed. Denitrification experiments were conducted as outlined in Example 3. Results are shown in the following table:

| | Waste Water Extract | | |
|---|---|---|---|
| Isolate | Rate (mM hr$^{-1}$) | DO (ppm) T = 0 | DO (ppm) T = 24 |
| *B. subtilis* (strain 1) | −0.009 | 7.7 | 6.4 |
| *B. subtilis* (strain 2) | | | |
| *B. mojavensis* | 0.011 | 8.5 | 6.8 |
| *B. pumilus* | −0.110 | 7.7 | 5.8 |

-continued

Waste Water Extract

| Isolate | Rate (mM hr$^{-1}$) | DO (ppm) T = 0 | DO (ppm) T = 24 |
|---|---|---|---|
| B. licheniformis | −0.112 | 7.3 | 5.4 |
| P. acidilactici | −0.430 | 7.3 | 5.4 |
| P. pentosaceus | −0.223 | 7.2 | 6.2 |
| L. plantarum | −0.001 | 7.0 | 5.9 |

Rates of denitrification are estimates of the pseudo-first order rate based on a regression analysis of the data in $\ln(C_t/C_0)/t$ form. Negative values indicate degradation of nitrate over time. Positive values indicate nitrate production over time.

Example 5: Denitrification Experiments with Mixed Microbial Samples in Waste Water Extract Bacterial isolates showing the highest rates of denitrification in simulated (Example 3) and/or actual (Example 4) wastewater were mixed together and evaluated for denitrification ability in waste water extracts. *Bacillus pumilus*, *Bacillus licheniformis*, . . . were mixed together in the ratio 1:1:1 . . . and tested according to the protocol outlined in Example 4. The starting DO was 7.2 ppm and the DO after 24 hours was 5.8 ppm. The initial nitrate level was 25 mg/L. The rate of nitrate degradation for this mixture was −0.115 mM/hr.

Example 6

Inoculums of various bacterial isolates were added to duplicate wastewater reactor flasks, from which a 15 mL sample (T=0) was immediately, aseptically removed using a sterile serological pipette and stored inside a sterile, screw-capped 15 mL centrifuge tube. Reactor flasks were then placed inside an incubator/shaker set to 40° C. Flasks were periodically removed for sampling as described above at hours 2, 3, 4, 5, 6 and 24. Sample tubes were centrifuged at 6,000×g for 10 minutes to remove suspended cells, which may have interfered with spectrophotometric analysis. Following centrifugation, 5 mL aliquots were removed from the tube using an autopipettor and dispensed into 20 mL scintillation vials for colorimetric analysis.

Nitrate concentrations were determined colorimetrically using a nitration of salicylic acid method (University of Wisconsin, Dept. of Agronomy, 1975). Sample aliquots of 0.2 mL were dispensed into 25-mL Erlenmeyer flasks, which were then mixed with 0.8 mL of concentrated sulfuric acid ($H_2SO_4$). A blank was also made with distilled water, mineral medium, or wastewater, depending on the medium of the samples. The samples were left for 20 minutes, and then 19 mL of 2M NaOH were added. The samples were cooled to room temperature and then analyzed for absorbance with an Agilent Cary-60 spectrophotometer calibrated at 410 nm (y=0.00143x-0.00431; $r^2$=0.999).

A commercial dissolved oxygen test kit (LaMotte) was used as directed to titrate dissolved oxygen within the reactor flasks. These data are approximate trends for qualitative comparisons. Samples were not kept air-tight during reaction flask incubation.

Results from the waste water samples are summarized in FIG. 1.

Example 7

Inoculum Procedure

The inoculum for all partial aeration experiments was started by mixing 15 g of BD BBL™ Dehydrated Culture Media: Trypticase Soy Broth with 500 mL of DI water in a 1 L Erlenmeyer flask. The solution was stirred with a magnetic stir bar for approximately 5 minutes until all media had dissolved. The mixture was then autoclaved at 121° C. for 15 minutes. The broth was allowed to cool at ambient temperature until safe to handle (approximately 45 minutes). A microbial mixture comprising *Bacillus subtilis*, *Bacillus pumilus*, *Bacillus licheniformis*, *Bacillus amyloliquefaciens*, *Pediococcus acidilactici*, *Pediococcus pentosaceus*, and *Lactobacillus plantarum* was vigorously swirled in the sterile culture media for approximately 30 seconds. The flask was then capped with a sterile, breathable lid and placed in a 35° C. incubator for approximately 18 hours before use in the partial aeration experiment.

Partial Aeration Experiment Procedure

Figure 2:
FIG. 2 is a photograph showing the partial aeration experiment set up in orbital shaker.

All partial aeration experiments were conducted in a 35° C. Thermo Forma Orbital Shaker. Two magnetic stir plates were placed in the shaker, along with a power strip, a YSI Pro-20 dissolved oxygen (DO) meter, and five aluminum 8"×8" square baking pans. The aluminum pans were deformed such that the remaining shaker floor surface area was reasonably covered. Each aluminum pan was filled to available capacity with DI water in order to slow evaporation in the shaker. An autoclaved 8"×8" square Pyrex® baking pan was placed on top of each stir plate. See FIG. 2 for clarification of setup.

Growth solution containing glucose ($C_6H_{12}O_6$), potassium phosphate monobasic ($KH_2PO_4$), potassium phosphate dibasic ($K_2HPO_4$), manganese chloride ($MnCl_2$), ferric chloride ($FeCl_3$), and sodium nitrate ($NaNO_3$) was prepared on day zero for each run. Two 2-liter bottles, each containing 1.35 L of growth solution were made up. Each bottle contained 1.35 L DI water with 1.5 g glucose [Fisher Chemical, Dextrose (D-Glucose) Anhydrous (Granular Powder/Certified ACS)], 0.375 g $KH_2PO_4$ [Fisher Chemical, Potassium Phosphate Monobasic (Crystalline/Certified ACS)], 0.375 g $K_2HPO_4$ [Fisher Chemical, Potassium Phosphate Dibasic Anhydrous (Crystalline Powder/USP)], 4 mg $MnCl_2.4H_2O$ (unknown source), 7.5 µL $FeCl_3$ [Fisher Chemical, Ferric Chloride Solution, 40% w/v (Laboratory)], and 227.7 mg $NaNO_3$ [Fisher Chemical, Sodium Nitrate (Crystalline/Certified ACS)].

A magnetic stir bar was placed in one bottle. Each bottle was foiled, loosely capped, and autoclaved for 24 minutes at 121° C. Each bottle was cooled at ambient temperature until safe to handle (approximately 1.5 hours). Then 150 mL of the bacterial inoculum was added to each bottle, for a combined volume of 1.5 L. The final nutrient concentration in the growth solution, after the addition of 150 mL of inoculum, is 1.5 g/L glucose, 0.25 g/L $KH_2PO_4$, 0.25 g/L $K_2HPO_4$, 2 mg/L $MnCl_2$, 2 mg/L $FeCl_3$, and 25 ppm $NO_3$—N, and any additional nutrients that remain from the TSB inoculum. Each bottle was gently mixed for approximately 15 seconds. The bottle with the stir bar was then carefully poured in to the Pyrex® dish on the left stir plate. The other bottle was carefully emptied in to the Pyrex® dish on the right stir plate. The left stir plate, containing the stir bar, was initially set to approximately 700 rpm.

Samples were taken at the beginning and approximately every 8 hours thereafter. Dissolved oxygen, nitrate and nitrite were measured. Nitrate and nitrite were measured with ion chromatography using a Dionex IonPac AG9-HC Guard Column (4×50 mm) and a Dionex IonPac AS9-HC Analytical Column (4×250 mm).

Figure 3:
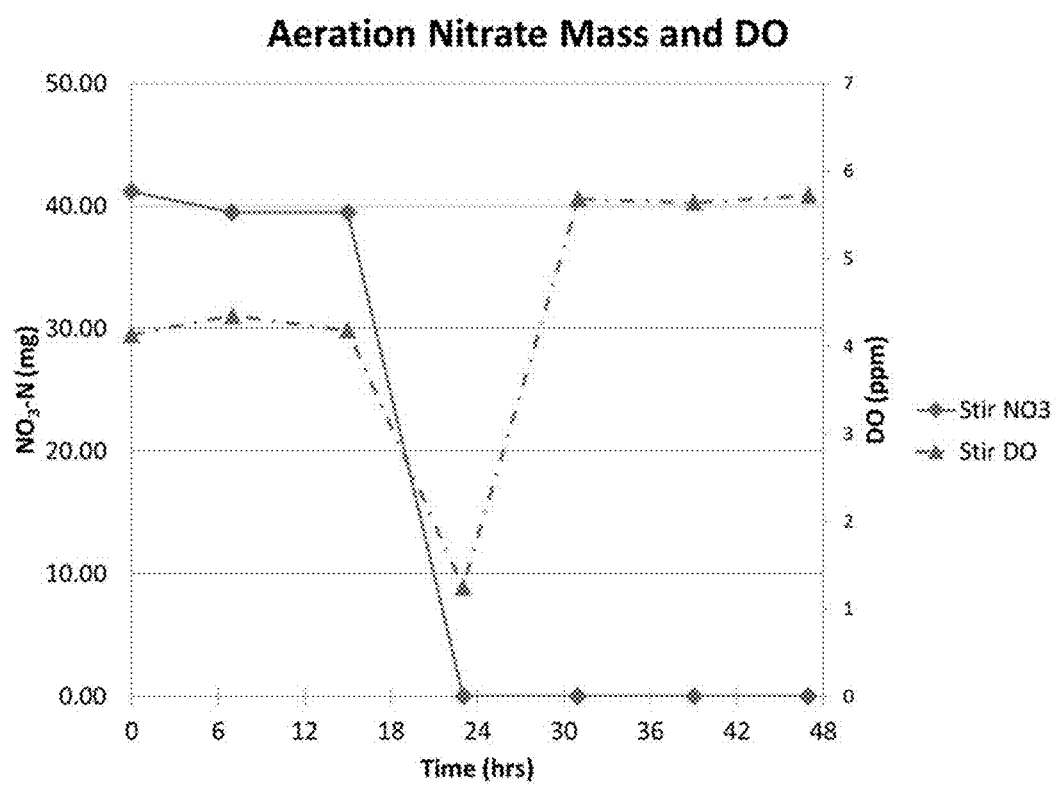
FIG. 3 is a graph showing nitrate removal and DO levels as a function of time for a starting concentration of 40 ppm nitrate.

FIG. 3 is a graph showing nitrate removal and DO levels as a function of time for a starting concentration of 40 ppm nitrate.

Figure 4:
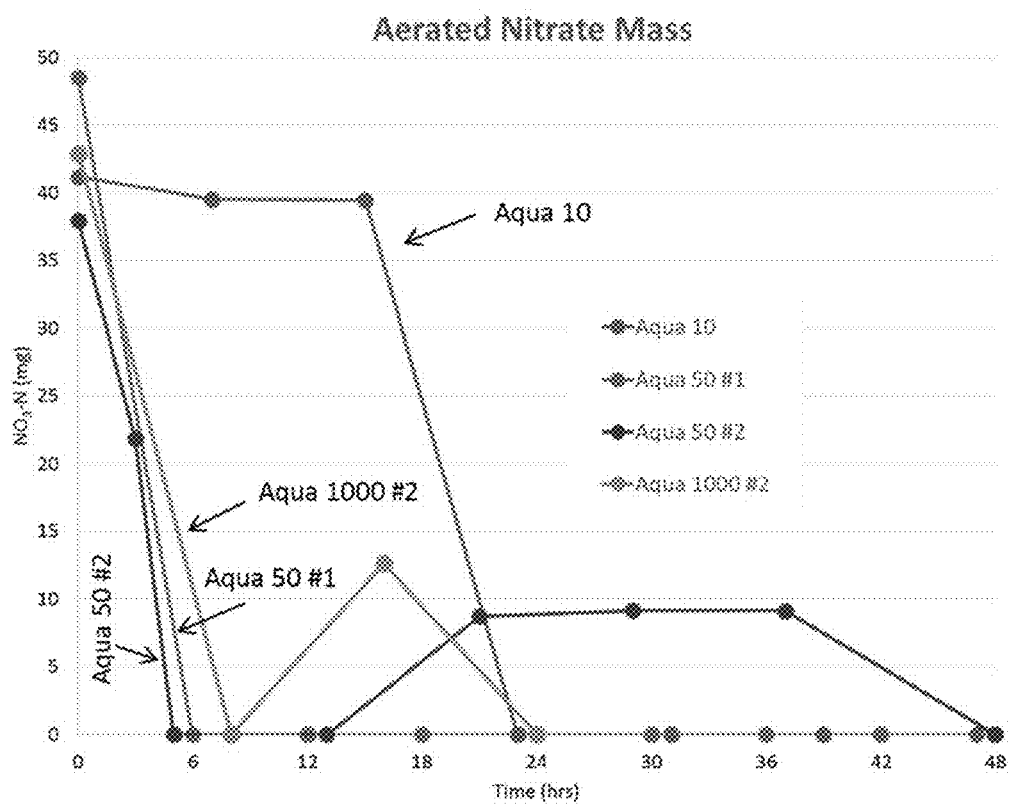
FIG. 4 is a graph showing aerobic nitrate removal as a function of time for various starting levels of nitrate (10-1000 ppm).

FIG. 4 is a graph showing aerobic nitrate removal as a function of time for various starting levels of nitrate (10-1000 ppm).

We claim:

1. A method of decreasing the nitrate level in an aqueous system having a dissolved oxygen level above 3 ppm, the method comprising contacting the aqueous system with a composition comprising:

a. a mixture of *Bacillus* bacterial species comprising *Bacillus subtilis, Bacillus licheniformis, Bacillus amyloliquefaciens*, and *Bacillus pumilus*; and b. a mixture of lactic acid bacteria comprising *Pediococcus acidilactici, Pediococcus pentosaceus*, and *Lactobacillus plantarum*, wherein the weight ratio of the *Bacilli* to the lactic acid bacteria ranges from 1:10 to 10:1, thereby decreasing the nitrate level in the aqueous system.

2. The method of claim 1, wherein the composition is embedded in a solid support.

3. The method of claim 1, wherein the *Bacillus subtilis* comprises *Bacillus subtilis* 34KLB.

4. The method of claim 1, wherein the *Bacillus subtilis* comprises *Mojavensis*.

5. The method of claim 1, wherein each of the lactic acid bacteria is present in equal amounts by weight.

6. The method of claim 1, wherein the composition further comprises an inert carrier.

7. The method of claim 6, wherein the inert carrier is anhydrous dextrose, dextrose monohydrate, dendritic salt, maltodextrin, rice bran, wheat bran, oat bran, soybean meal, rice hulls, or a mixture thereof.

8. The method of claim 1, wherein each of the *Bacillus* species is individually fermented aerobically to produce a culture, which is filtered, centrifuged, dried, and ground to an average particle size of about 200 microns.

9. The method of claim 1, wherein each of the lactic acid bacteria is fermented anaerobically to produce a culture, which is filtered, centrifuged, dried, and ground to an average particle size of about 200 microns.

10. The method of claim 1, wherein the composition has a moisture content of less than 5% and a final bacterial concentration of about $10^5$ to $10^{11}$ colony forming units (CFU) per gram of the composition.

11. The method of claim 6, wherein the inert carrier comprises about 75% to 95% (wt/wt) of the composition.

12. The method of claim 1, wherein the aqueous system is selected from the group consisting of municipal sewage, residential or commercial septic, industrial wastewater, a livestock waste water lagoon, an aquaculture pond, waste water from fruit and vegetable processing, waste water from brewery and distilling, a swimming pool, and a spa.

* * * * *

```
                        SEQUENCE LISTING

<160> NUMBER OF SEQ ID NOS: 1

<210> SEQ ID NO 1
<211> LENGTH: 1668
<212> TYPE: PRT
<213> ORGANISM: Bacillus subtilis

<400> SEQUENCE: 1

Ala Gly Cys Thr Cys Gly Gly Ala Thr Cys Cys Ala Cys Thr Ala Gly
1               5                   10                  15

Thr Ala Ala Cys Gly Gly Cys Cys Gly Cys Cys Ala Gly Thr Gly Thr
                20                  25                  30

Gly Cys Thr Gly Gly Ala Ala Thr Thr Cys Gly Cys Cys Cys Thr Thr
            35                  40                  45

Ala Gly Ala Ala Ala Gly Gly Ala Gly Gly Thr Gly Ala Thr Cys Cys
    50                  55                  60

Ala Gly Cys Cys Gly Cys Ala Cys Cys Thr Thr Cys Cys Gly Ala Thr
65                  70                  75                  80

Ala Cys Gly Gly Cys Thr Ala Cys Cys Thr Thr Gly Thr Thr Ala Cys
                85                  90                  95

Gly Ala Cys Thr Thr Cys Ala Cys Cys Cys Ala Ala Thr Cys Ala
                100                 105                 110

Thr Cys Thr Gly Thr Cys Cys Ala Cys Cys Thr Thr Cys Gly Gly
            115                 120                 125

Cys Gly Gly Cys Thr Gly Gly Cys Thr Cys Cys Ala Thr Ala Ala Ala
    130                 135                 140

Gly Gly Thr Thr Ala Cys Cys Thr Cys Ala Cys Cys Gly Ala Cys Thr
145                 150                 155                 160

Thr Cys Gly Gly Gly Thr Gly Thr Thr Ala Cys Ala Ala Ala Cys Thr
                165                 170                 175

Cys Thr Cys Gly Thr Gly Gly Thr Gly Thr Gly Ala Cys Gly Gly Gly
            180                 185                 190

Cys Gly Gly Thr Gly Thr Gly Thr Ala Cys Ala Ala Gly Cys Cys
    195                 200                 205

Cys Gly Gly Gly Ala Ala Cys Gly Thr Ala Thr Thr Cys Ala Cys Cys
210                 215                 220

Gly Cys Gly Gly Cys Ala Thr Gly Cys Thr Gly Ala Thr Cys Cys Gly
                225                 230                 235                 240

Cys Gly Ala Thr Thr Ala Cys Thr Ala Gly Cys Gly Ala Thr Thr Cys
                245                 250                 255

Cys Ala Gly Cys Thr Thr Cys Ala Cys Gly Cys Ala Gly Thr Cys Gly
            260                 265                 270

Ala Gly Thr Thr Gly Cys Ala Gly Ala Cys Thr Gly Cys Gly Ala Thr
    275                 280                 285

Cys Cys Gly Ala Ala Cys Thr Gly Ala Gly Ala Ala Cys Ala Gly Ala
            290                 295                 300

Thr Thr Thr Gly Thr Gly Arg Gly Ala Thr Thr Gly Gly Cys Thr Thr
305                 310                 315                 320

Ala Ala Cys Cys Thr Cys Gly Cys Gly Gly Thr Thr Thr Cys Gly Cys
```

-continued

```
                325                 330                 335

Thr Gly Cys Cys Cys Thr Thr Thr Gly Thr Thr Cys Thr Gly Thr Cys
            340                 345                 350
Cys Ala Thr Thr Gly Thr Ala Gly Cys Ala Cys Gly Thr Gly Thr Gly
        355                 360                 365

Thr Ala Gly Cys Cys Cys Ala Gly Gly Thr Cys Ala Thr Ala Ala Gly
    370                 375                 380

Gly Gly Gly Cys Ala Thr Gly Ala Thr Gly Ala Thr Thr Thr Gly Ala
385                 390                 395                 400

Cys Gly Thr Cys Ala Thr Cys Cys Cys Cys Ala Cys Cys Thr Thr Cys
                405                 410                 415

Cys Thr Cys Cys Gly Gly Thr Thr Thr Gly Thr Cys Ala Cys Cys Gly
            420                 425                 430
Gly Cys Ala Gly Thr Cys Ala Cys Cys Thr Thr Ala Gly Ala Gly Thr
        435                 440                 445
Gly Cys Cys Cys Ala Ala Cys Thr Gly Ala Ala Thr Gly Cys Thr Gly
    450                 455                 460

Gly Cys Ala Ala Cys Thr Ala Ala Gly Ala Thr Cys Ala Ala Gly Gly
465                 470                 475                 480

Gly Thr Thr Gly Cys Gly Cys Thr Cys Gly Thr Thr Gly Cys Gly Gly
                485                 490                 495

Gly Ala Cys Thr Thr Ala Ala Cys Cys Cys Ala Ala Cys Ala Thr Cys
            500                 505                 510

Thr Cys Ala Cys Gly Ala Cys Ala Cys Gly Ala Gly Cys Thr Gly Ala
        515                 520                 525

Cys Gly Ala Cys Ala Ala Cys Cys Ala Thr Gly Cys Ala Cys Cys Ala
    530                 535                 540

Cys Cys Thr Gly Thr Cys Ala Cys Thr Cys Thr Gly Cys Cys Cys Cys
545                 550                 555                 560

Cys Gly Ala Ala Gly Gly Gly Gly Ala Cys Gly Thr Cys Cys Thr Ala
                565                 570                 575

Thr Cys Thr Cys Thr Ala Gly Gly Ala Thr Thr Gly Thr Cys Ala Gly
            580                 585                 590

Ala Gly Gly Ala Thr Gly Thr Cys Ala Ala Gly Ala Cys Cys Thr Gly
        595                 600                 605

Gly Thr Ala Ala Gly Gly Thr Thr Cys Thr Thr Cys Gly Cys Gly Thr
    610                 615                 620

Thr Gly Cys Thr Thr Cys Gly Ala Ala Thr Thr Ala Ala Ala Cys Cys
625                 630                 635                 640

Ala Cys Ala Thr Gly Cys Thr Cys Cys Ala Cys Cys Gly Cys Thr Thr
                645                 650                 655

Gly Thr Gly Cys Gly Gly Gly Cys Cys Cys Cys Cys Gly Thr Cys Ala
            660                 665                 670

Ala Thr Thr Cys Cys Thr Thr Thr Gly Ala Gly Thr Thr Thr Cys Ala
        675                 680                 685

Gly Thr Cys Thr Thr Gly Cys Gly Ala Cys Cys Gly Thr Ala Cys Thr
    690                 695                 700

Cys Cys Cys Cys Ala Gly Gly Cys Gly Gly Ala Gly Thr Gly Cys Thr
705                 710                 715                 720

Thr Ala Ala Thr Gly Cys Gly Thr Thr Ala Gly Cys Thr Gly Cys Ala
                725                 730                 735

Gly Cys Ala Cys Thr Ala Ala Ala Gly Gly Gly Gly Cys Gly Gly Ala
            740                 745                 750
```

```
Ala Ala Cys Cys Cys Cys Thr Ala Ala Cys Ala Cys Thr Thr Ala
        755                 760                 765
Gly Cys Ala Cys Thr Cys Ala Thr Cys Gly Thr Thr Thr Ala Cys Gly
    770                 775                 780
Gly Cys Gly Thr Gly Gly Ala Cys Thr Ala Cys Cys Ala Gly Gly Gly
785                 790                 795                 800
Thr Ala Thr Cys Thr Ala Ala Thr Cys Cys Thr Gly Thr Thr Cys Gly
                805                 810                 815
Cys Thr Cys Cys Cys Cys Ala Cys Gly Cys Thr Thr Thr Cys Gly Cys
                820                 825                 830
Thr Cys Cys Thr Cys Ala Gly Cys Gly Thr Cys Ala Gly Thr Thr Ala
                835                 840                 845
Cys Ala Gly Ala Cys Cys Ala Gly Ala Gly Ala Gly Thr Cys Gly Cys
            850                 855                 860
Cys Thr Thr Cys Gly Cys Cys Ala Cys Thr Gly Gly Thr Gly Thr Thr
865                 870                 875                 880
Cys Cys Thr Cys Cys Ala Cys Ala Thr Cys Thr Cys Thr Ala Cys Gly
                885                 890                 895
Cys Ala Thr Thr Thr Cys Ala Cys Cys Gly Cys Thr Ala Cys Ala Cys
                900                 905                 910
Gly Thr Gly Gly Ala Ala Thr Thr Cys Cys Ala Cys Thr Cys Thr Cys
                915                 920                 925
Cys Thr Cys Thr Thr Cys Thr Gly Cys Ala Cys Thr Cys Ala Ala Gly
            930                 935                 940
Thr Thr Cys Cys Cys Cys Ala Gly Thr Thr Thr Cys Cys Ala Ala Thr
945                 950                 955                 960
Gly Ala Cys Cys Cys Thr Cys Cys Cys Gly Gly Thr Thr Gly Ala
            965                 970                 975
Gly Cys Cys Gly Gly Gly Gly Cys Thr Thr Thr Cys Ala Cys Ala
            980                 985                 990
Thr Cys Ala Gly Ala Cys Thr Thr  Ala Ala Gly Ala Ala  Ala Cys Cys
            995                 1000                1005
Gly Cys  Cys Thr Gly Cys Gly Ala Gly Cys Cys Cys  Thr Thr Thr
    1010                1015                1020
Ala Cys  Gly Cys Cys Cys Ala  Ala Thr Ala Ala Thr  Thr Cys Cys
    1025                1030                1035
Gly Gly  Ala Cys Ala Ala Cys  Gly Cys Thr Thr Gly  Cys Cys Ala
    1040                1045                1050
Cys Cys  Thr Ala Cys Gly Thr  Ala Thr Thr Ala Cys  Cys Gly Cys
    1055                1060                1065
Gly Gly  Cys Thr Gly Cys Thr  Gly Gly Cys Ala Cys  Gly Thr Ala
    1070                1075                1080
Gly Thr  Thr Ala Gly Cys Cys  Gly Thr Gly Gly Cys  Thr Thr Thr
    1085                1090                1095
Cys Thr  Gly Gly Thr Thr Ala  Gly Gly Thr Ala Cys  Cys Gly Thr
    1100                1105                1110
Cys Ala  Ala Gly Gly Thr Gly  Cys Cys Gly Cys Cys  Cys Thr Ala
    1115                1120                1125
Thr Thr  Thr Gly Ala Ala Cys  Gly Gly Cys Ala Cys  Thr Thr Gly
    1130                1135                1140
Thr Thr  Cys Thr Thr Cys Cys  Cys Thr Ala Ala Cys  Ala Ala Cys
    1145                1150                1155
```

-continued

```
Ala Gly Ala Gly Cys Thr Thr Thr Ala Cys Gly Ala Thr Cys Cys
    1160              1165              1170

Gly Ala Ala Ala Ala Cys Cys Thr Thr Cys Ala Thr Cys Ala Cys
    1175              1180              1185

Thr Cys Ala Cys Gly Cys Gly Gly Cys Gly Thr Thr Gly Cys Thr
    1190              1195              1200

Cys Cys Gly Thr Cys Ala Gly Ala Cys Thr Thr Cys Gly Thr
    1205              1210              1215

Cys Cys Ala Thr Thr Gly Cys Gly Gly Ala Ala Gly Ala Thr Thr
    1220              1225              1230

Cys Cys Cys Thr Ala Cys Thr Gly Cys Thr Gly Cys Cys Thr Cys
    1235              1240              1245

Cys Cys Gly Thr Ala Gly Gly Ala Gly Thr Cys Thr Gly Gly Gly
    1250              1255              1260

Cys Cys Gly Thr Gly Thr Cys Thr Cys Ala Gly Thr Cys Cys Cys
    1265              1270              1275

Ala Gly Thr Gly Thr Gly Gly Cys Cys Gly Ala Thr Cys Ala Cys
    1280              1285              1290

Cys Cys Thr Cys Thr Cys Ala Gly Gly Thr Cys Gly Gly Cys Thr
    1295              1300              1305

Ala Cys Gly Cys Ala Thr Cys Gly Thr Cys Gly Cys Cys Thr Thr
    1310              1315              1320

Gly Gly Thr Gly Ala Gly Cys Cys Gly Thr Thr Ala Cys Cys Thr
    1325              1330              1335

Cys Ala Cys Cys Ala Ala Cys Thr Ala Gly Cys Thr Ala Ala Thr
    1340              1345              1350

Gly Cys Gly Cys Cys Gly Cys Gly Gly Gly Thr Cys Cys Ala Thr
    1355              1360              1365

Cys Thr Gly Thr Ala Ala Gly Thr Gly Thr Ala Gly Cys Gly Cys
    1370              1375              1380

Gly Ala Ala Gly Cys Cys Ala Cys Cys Thr Thr Thr Thr Ala Thr
    1385              1390              1395

Gly Thr Cys Thr Gly Ala Ala Cys Cys Ala Thr Gly Cys Gly Gly
    1400              1405              1410

Thr Thr Cys Ala Gly Ala Cys Ala Ala Cys Cys Ala Thr Cys Cys
    1415              1420              1425

Gly Gly Thr Ala Thr Thr Ala Gly Cys Cys Cys Cys Gly Gly Thr
    1430              1435              1440

Thr Thr Cys Cys Cys Gly Gly Ala Gly Thr Thr Ala Thr Cys Cys
    1445              1450              1455

Cys Ala Gly Thr Cys Thr Thr Ala Cys Ala Gly Gly Cys Ala Gly
    1460              1465              1470

Gly Thr Thr Ala Cys Cys Cys Ala Cys Gly Thr Gly Thr Thr Ala
    1475              1480              1485

Cys Thr Cys Ala Cys Cys Cys Gly Thr Cys Cys Gly Cys Cys Gly
    1490              1495              1500

Cys Thr Ala Ala Cys Ala Thr Cys Ala Gly Gly Ala Gly Cys
    1505              1510              1515

Ala Ala Gly Cys Thr Cys Cys Cys Ala Thr Cys Thr Gly Thr Cys
    1520              1525              1530

Cys Gly Cys Thr Cys Gly Ala Cys Thr Thr Gly Cys Ala Thr Gly
    1535              1540              1545

Thr Ala Thr Thr Ala Gly Gly Cys Ala Cys Gly Cys Cys Gly Cys
```

-continued

| | | | | | | | | | | | | | | |
|---|---|---|---|---|---|---|---|---|---|---|---|---|---|---|
| | 1550 | | | | | 1555 | | | | | 1560 | | | |
| Cys | Ala | Gly | Cys | Gly | Thr | Thr | Cys | Gly | Thr | Cys | Cys | Thr | Gly | Ala |
| | 1565 | | | | | 1570 | | | | | 1575 | | | |
| Gly | Cys | Cys | Ala | Thr | Gly | Ala | Ala | Cys | Ala | Ala | Ala | Cys | Thr | Cys |
| | 1580 | | | | | 1585 | | | | | 1590 | | | |
| Thr | Ala | Ala | Gly | Gly | Gly | Cys | Gly | Ala | Ala | Thr | Thr | Cys | Thr | Gly |
| | 1595 | | | | | 1600 | | | | | 1605 | | | |
| Cys | Ala | Gly | Ala | Thr | Ala | Thr | Cys | Cys | Ala | Thr | Cys | Ala | Cys | Ala |
| | 1610 | | | | | 1615 | | | | | 1620 | | | |
| Cys | Thr | Gly | Gly | Cys | Gly | Gly | Cys | Cys | Gly | Cys | Thr | Cys | Gly | Ala |
| | 1625 | | | | | 1630 | | | | | 1635 | | | |
| Gly | Cys | Ala | Thr | Gly | Cys | Ala | Thr | Cys | Thr | Ala | Gly | Ala | Gly | Gly |
| | 1640 | | | | | 1645 | | | | | 1650 | | | |
| Gly | Cys | Cys | Cys | Ala | Ala | Thr | Cys | Gly | Cys | Cys | Cys | Thr | Ala | Thr |
| | 1655 | | | | | 1660 | | | | | 1665 | | | |